United States Patent
Kuenen et al.

(10) Patent No.: US 11,896,422 B2
(45) Date of Patent: Feb. 13, 2024

(54) SYSTEMS AND METHOD FOR PERFORMING PULSE WAVE VELOCITY MEASUREMENTS

(71) Applicant: KONINKLIJKE PHILIPS N.V., Eindhoven (NL)

(72) Inventors: Maarten Petrus Joseph Kuenen, Veldhoven (NL); Arjen Van Der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/269,672

(22) PCT Filed: Aug. 13, 2019

(86) PCT No.: PCT/EP2019/071634
§ 371 (c)(1),
(2) Date: Feb. 19, 2021

(87) PCT Pub. No.: WO2020/038757
PCT Pub. Date: Feb. 27, 2020

(65) Prior Publication Data
US 2021/0338193 A1 Nov. 4, 2021

(30) Foreign Application Priority Data
Aug. 21, 2018 (EP) ..................... 18189871

(51) Int. Cl.
*A61B 8/06* (2006.01)
*A61B 8/12* (2006.01)
(Continued)

(52) U.S. Cl.
CPC .................. *A61B 8/06* (2013.01); *A61B 8/12* (2013.01); *A61B 8/4494* (2013.01); *A61B 8/488* (2013.01);
(Continued)

(58) Field of Classification Search
None
See application file for complete search history.

(56) References Cited

U.S. PATENT DOCUMENTS 5,535,747 A * 7/1996 Katakura ................. A61B 8/04
600/438
5,997,479 A 12/1999 Savord
(Continued)

FOREIGN PATENT DOCUMENTS

EP 3263018 A1 1/2018
WO WO-2015107993 A1 * 7/2015 ........... A61B 5/0285
(Continued)

OTHER PUBLICATIONS

Wang et al., "Noninvasive Method for Measuring Local Pulse Wave Velocity by Dual Pulse Wave Doppler: In Vitro and In Vivo Studies," (Mar. 18, 2015), PLoS ONE, 2015, vol. 10 (3), p. e0120482-e0120482. (Year: 2015).*
(Continued)

*Primary Examiner* — Joel Lamprecht
*Assistant Examiner* — Ashish S Jasani

(57) ABSTRACT

The invention provides a system and a method for calculating a pulse wave velocity based on a plurality of intravascular ultrasonic pulses directed along a vessel. For each ultrasonic pulse, a plurality of echoes is received from a plurality of distances along the vessel. A first ultrasound Doppler signal is received from a first distance from the pulse origin and a second ultrasound Doppler signal from a second distance from the pulse origin. A first and second flow velocity metric is obtained based on the first and second ultrasound Doppler signal, respectively. The pulse wave velocity is calculated based on the time delay, which is based on the first flow velocity metric and the second flow velocity metric.

15 Claims, 7 Drawing Sheets

(51) Int. Cl.
*A61B 8/00* (2006.01)
*A61B 8/08* (2006.01)
*G01S 15/89* (2006.01)

(52) U.S. Cl.
CPC ...... *G01S 15/8915* (2013.01); *G01S 15/8979* (2013.01); *A61B 8/4488* (2013.01)

(56) References Cited

U.S. PATENT DOCUMENTS

| | | | |
|---|---|---|---|
| 6,013,032 A | 1/2000 | Savord | |
| 6,193,669 B1* | 2/2001 | Degany | A61B 5/02014 600/561 |
| 6,261,233 B1* | 7/2001 | Kantorovich | A61B 8/06 600/454 |
| 6,283,919 B1 | 9/2001 | Roundhill | |
| 6,443,896 B1 | 9/2002 | Detmer | |
| 6,458,083 B1 | 10/2002 | Jago | |
| 6,530,885 B1 | 3/2003 | Entrekin | |
| 6,623,432 B2 | 9/2003 | Powers | |
| 2004/0220474 A1 | 11/2004 | Abend | |
| 2005/0187468 A1 | 8/2005 | Atlas | |
| 2008/0081994 A1* | 4/2008 | Kim | A61B 5/0285 600/438 |
| 2010/0113949 A1* | 5/2010 | Sathyanarayana | A61B 8/12 600/500 |
| 2020/0146641 A1 | 5/2020 | Van Der Horst | |

FOREIGN PATENT DOCUMENTS

| | | | | |
|---|---|---|---|---|
| WO | 2017198800 A1 | 11/2017 | | |
| WO | 2017198871 A1 | 11/2017 | | |
| WO | WO-2017198800 A1 * | 11/2017 | .......... | A61B 5/0035 |
| WO | WO-2017198867 A1 * | 11/2017 | .......... | A61B 5/0084 |

OTHER PUBLICATIONS

International Search Report and Written Opinion for PCT/EP2019/071634, dated Oct. 4, 2019.

Harbaoui et al "Development of Coronary Pulse Wave Velocity: New Pathophysiological Insight into Coronary Artery Disease", Journal of American Heart Association, 2017.

Loupas et al An Axial Velocity Estimator for Ultrasound Blood Flow Imaging, based on a Full Evaluation of the Dop0pler Equation by Means of a Two-Dimensional Autocorrelation Approach, IEEE Transactions on Ultrasonics, Ferroelectrics, and Frequency Control, vol. 42, No. 4, Jul. 1995.

Kasai et al "Real-Time Two-Dimensional Blood FLow Imaging using an Autocorrelation Technique", IEEE Transactions on Sonics and Ultrasonics, vol. SU-32, No. 3, May 1985.

Davies, Justin "Systematic Evaluation of Haemodynamic Parameters to Predict Haemodynamic Responders to Renal Artery Denervation", Imperial College Longon, EUROPCR, 2016.

* cited by examiner

SYSTEMS AND METHOD FOR PERFORMING PULSE WAVE VELOCITY MEASUREMENTS

CROSS-REFERENCE TO PRIOR APPLICATIONS

This application is the U.S. National Phase application under 35 U.S.C. § 371 of International Application No. PCT/EP2019/071634, filed on Aug. 13, 2019, which claims the benefit of European Patent Application No. 18189871.9, filed on Aug. 21, 2018. These applications are hereby incorporated by reference herein.

FIELD OF THE INVENTION

This invention relates to systems for measuring pulse wave velocity, and in particular to intravascular systems for measuring pulse wave velocity.

BACKGROUND OF THE INVENTION

Arterial stiffening is an important risk factor for cardiovascular disease. Arterial stiffness increases with aging and various disease states, including: hypertension; hypercholesterolemia; diabetes mellitus; obesity; smoking; and kidney disease.

A commonly used parameter to assess the stiffness of a vessel is pulse wave velocity (PWV). PWV is the transmission speed of pressure/flow waves, for example generated by a beating heart, through the arteries. The PWV is determined by the ability of the vessel to expand, i.e. distensibility, D, according to the following relation:

$$PWV = \sqrt{\frac{1}{\rho D}}, \text{ with } D = \frac{dV}{VdP}$$

where: V is the vascular volume; P the pressure within the vessel; and $\rho$ is the blood density. From this relation, the Moens-Korteweg equation can be derived:

$$PWV = \sqrt{\frac{E \cdot h}{d \cdot \rho}}$$

where: E is the Young's modulus; d is the vessel diameter; and h is the wall thickness. By assessing the PWV, the stiffness of the arteries may be quantified. A typical value for PWV in an artery is 10 m/s, which is an order of magnitude higher than the velocity of the blood particles.

The relevance of the local PWV in arteries in guiding treatment is clear from recent studies, such as: Finegold et al. *Systematic evaluation of haemodynamic parameters to predict haemodynamic responders to renal artery denervation*, abstract EuroPCR, 2016. This paper indicates that the PWV inside the main renal artery pre-treatment is predictive of the outcome of renal denervation in patients with resistive hypertension. Harbaoui et al. *Development of Coronary Pulse Wave Velocity: New Pathophysiological Insight Into Coronary Artery Disease*, J Am Heart Assoc. 2017, indicates that low coronary PWV is associated with acute coronary syndromes, indicating a relation between plaque vulnerability and arterial stiffness.

As the pressure/flow waves travel very quickly through the vessels, the PWV is most commonly determined over relatively large distances in the vasculature, such as from the brachial artery to the ankle. In this way, the average stiffness of the vessels in between the measurements locations is determined.

In the last decade, further local PWV measurements have been developed. For superficial arteries external ultrasound can be used to assess PWV. Another approach that is also suitable for local assessment of the PWV in deeper arteries is using sensor-equipped catheters. For example, two or more pressure sensors on a catheter at known distances (x) can be used to determine the time difference ($\Delta t$) of the passing waves as:

$$PWV = \frac{x}{\Delta t}$$

Currently, these catheter-based measurements are typically performed in the aorta, which is relatively long and has a large diameter. For shorter arteries, which are typically also much smaller in diameter, the technical requirements (such as sample frequency, synchronization and the like) of the measurement devices are more challenging.

Moreover, all solutions proposed require at least two sensors (such as dual-pressure sensor, or a pressure and flow sensor). This increases the complexity and cost of the PWV measurement device.

There is therefore a need for a PWV measurement system capable of performing PWV measurements in smaller arteries without requiring significant additional hardware.

SUMMARY OF THE INVENTION

The invention is defined by the claims.

According to examples in accordance with an aspect of the invention, there is provided a method for calculating a pulse wave velocity, the method comprising:

generating a plurality of intravascular ultrasonic pulses, at a pulse origin, directed along a central axis of a vessel;

for each ultrasonic pulse, receiving a plurality of echoes from a plurality of distances along the central axis of the vessel;

obtaining a first ultrasound Doppler signal from a first distance from the pulse origin and a second ultrasound Doppler signal from a second distance from the pulse origin;

calculating a time delay based on the first ultrasound Doppler signal and the second ultrasound Doppler signal; and calculating the pulse wave velocity based on the time delay.

This method provides for calculating the pulse wave velocity within a vessel using a single sensor (such as an ultrasound transducer).

In pulsed Doppler processing, a Doppler signal is obtained from the received echo signals at various measurement depths, which correspond to certain time delays after each pulse was transmitted. The measurement depth and time delay are linked by a known speed of sound in blood. Each transmission will provide one sample to the Doppler signal at each measurement depth.

As the first and second measurement distances are known, and may be predetermined based on system restrictions to result in the highest possible signal quality, the time delay relating to the received Doppler signals between the two measurement locations may be used to calculate the pulse wave velocity.

In other words, the Doppler signals in a (blood) vessel are measured dynamically in at least two locations along the main axis of a vessel of interest. The pulse wave velocity is then calculated from the time it takes for the Doppler signal profile to travel from the first location to a second (or other) location. The advantage is that the velocity signal profile does not need to be identical (e.g. in amplitude, width), because it is sufficient if the velocity profiles show similarity, as for the PWV calculation is only the time interval is necessary for the velocity profile to travel from the first to the second location. In other words, a velocity profile measured in a first location, can be intercepted (measured) at the second location having slightly different profile due to a misalignment of the intravascular device with respect to the longitudinal axis of the blood vessel. This means that misalignment of the intravascular device with respect to the longitudinal axis of the vessel is tolerated as far as both locations of velocity measurements are taking place within the lumen of the vessel.

In an embodiment, the calculation of the time delay comprises performing cross-correlation between the first ultrasound Doppler signal and the second ultrasound Doppler signal.

In this way, the time delay may be determined by acquiring the sample time delay at which the Doppler signals between the first and second measurement locations provide the highest correlation.

In an embodiment, the calculating of the time delay comprises:

obtaining a first flow velocity metric based on the first ultrasound Doppler signal;

obtaining a second flow velocity metric based on the second ultrasound Doppler signal; and calculating the time delay based on the first flow velocity metric and the second flow velocity metric.

In this way, it is possible to calculate the time delay based on a first and second velocity flow metric derived from the first and second ultrasound Doppler signal, respectively.

In an arrangement, the first flow velocity metric comprises a first average velocity and the second flow velocity metric comprises a second average velocity.

The velocities at the measurement locations may be averaged over time in order to improve the accuracy of the time delay calculation.

In another arrangement, the first flow velocity metric comprises a first distribution of flow velocities and the second flow velocity metric comprises a second distribution of flow velocities.

The flow velocity distributions provide the full range of velocities measured at the measurement locations over a number of transmissions, thereby providing a full representation of the vessel measurements.

In a further arrangement, obtaining of a first distribution of flow velocities comprises obtaining a first frequency spectrum and obtaining of a second distribution of flow velocities comprises obtaining a second frequency spectrum.

Flow velocity distributions are typically acquired as a frequency spectrum. This may allow for analysis to be performed across frequency bins, which would be equivalent to a given velocity value or range of values. The size of the frequency bins may be altered based on system limitations.

In a further, or other, embodiment, the calculation of the time delay comprises:

for each velocity value of the first distribution of flow velocities and second distribution of flow velocities, calculating an individual time delay; and calculating an average time delay based on the individual time delays.

In this way, every measured velocity may be taken into account. By averaging the velocities over the distribution, it is possible to reduce the impact of erroneous measurements on the accuracy of the final result.

In a further, or other, embodiment, the calculation of the time delay comprises:

extracting a first feature of the first distribution of flow velocities;

extracting a second feature of the second distribution of flow velocities; and calculating a time delay based on the first feature and the second feature.

In this way, aspects of the velocity distributions which do not correspond to blood flow, such as slow velocities representing wall motion rather than flow, may be removed from the calculation, thereby increasing the accuracy of the final result.

In a further embodiment, the first feature is a first plurality of features and the second feature is a second plurality of features.

By taking multiple features into account, the accuracy of the final calculation is increased.

In a yet further embodiment, the first and second features comprise one or more of:

an instantaneous peak velocity;
a pulse onset;
a peak time;
a maximum acceleration; and
an instantaneous average velocity.

In an embodiment, the calculation of the time delay comprises performing cross-correlation between the first distribution of flow velocities and the second distribution of flow velocities.

In an embodiment, the method further comprises obtaining a pressure metric and wherein the calculation of the pulse wave velocity is based on the time delay and the pressure metric.

By taking multiple methods of calculating pulse wave velocity into account, the accuracy of the final calculation may be increased.

In an arrangement, the directing of the plurality of intravascular ultrasonic pulses along the central axis of the vessel comprises electronic beam steering and/or electronic beam focusing.

According to examples in accordance with an aspect of the invention, there is provided a computer program comprising computer program code means which is adapted, when said computer program is run on a computer, to implement the method described above.

According to examples in accordance with an aspect of the invention, there is provided an ultrasound system for performing intravascular pulse wave velocity measurements, the system comprising:

an intravascular ultrasound unit adapted to:

generate a plurality of intravascular ultrasonic pulses, at a pulse origin, directed along a central axis of a vessel; and for each ultrasonic pulse, receive a plurality of echoes from a plurality of distances along the central axis of the vessel; and a processor adapted to:
obtain a first ultrasound Doppler signal from a first distance from the pulse origin and a second ultrasound Doppler signal from a second distance from the pulse origin;
calculate a time delay based on the first ultrasound Doppler signal and the second ultrasound Doppler signal; and
calculate the pulse wave velocity based on the time delay.

In an embodiment, the intravascular ultrasound unit comprises:
a single ultrasound transducer element;
an array of ultrasound transducer elements; or
a first intravascular ultrasound element and a second intravascular ultrasound element, wherein the first intravascular ultrasound element and the second intravascular ultrasound element are spatially independent of each other.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

Figure 1:
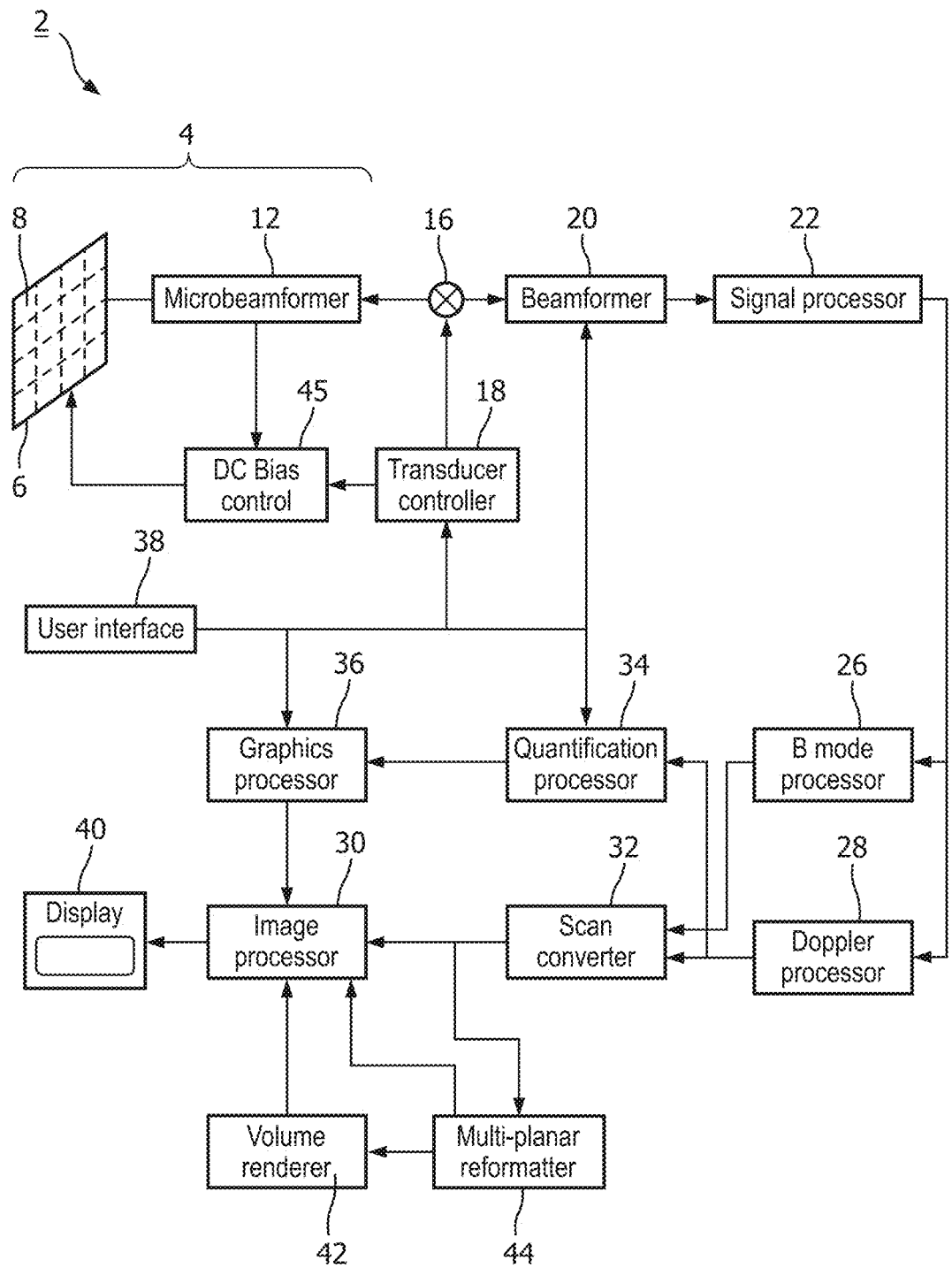
FIG. 1 shows an ultrasound diagnostic imaging system to explain the general operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for calculating a pulse wave velocity based on a plurality of intravascular ultrasonic pulses directed along a central axis of a vessel. For each ultrasonic pulse, a plurality of echoes is received from a plurality of distances along the central axis of the vessel. A first ultrasound Doppler signal is received from a first distance from the pulse origin and a second ultrasound Doppler signal from a second distance from the pulse origin.

A first and second flow velocity metric is obtained based on the first and second ultrasound Doppler signal, respectively. The pulse wave velocity is calculated based on the time delay, which is based on the first flow velocity metric and the second flow velocity metric.

The general operation of an exemplary ultrasound system will first be described, with reference to FIG. 1, and with emphasis on the signal processing function of the system since this invention relates to the processing by the system of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below.

Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition:

plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing.

The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
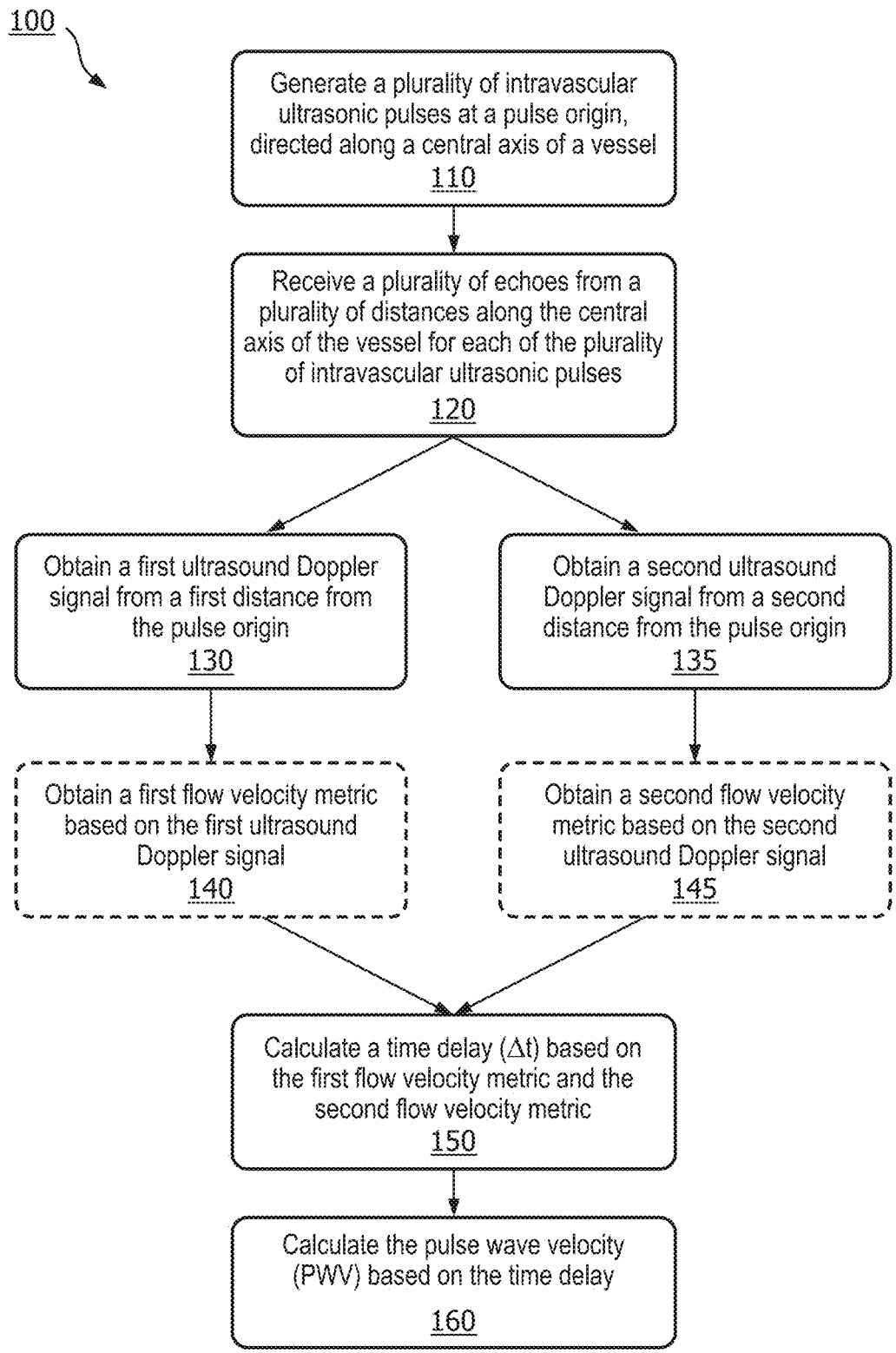
FIG. 2 shows a method of the invention.

FIG. 2 shows a method 100 for calculating a pulse wave velocity.

In step 110, a plurality of intravascular ultrasonic pulses is generated at a pulse origin, directed along a central axis of a vessel.

Blood flow velocity measurements can be performed by a pulsed-wave Doppler ultrasound method, which allows the locations of interest to be measured with a single ultrasound transmission and, consequently, by just a single sensor. This requires the ultrasound transducer to be in line with the vessel's main axis, which can typically best be achieved by means of an intravascular approach.

In other words, a single ultrasound transducer may be inserted into a vessel to perform blood flow measurements. This may be performed using a guidewire or catheter with an ultrasound transducer at its tip, aimed along the vessel's main axis.

In step 120, for each ultrasonic pulse, a plurality of echoes is received from a plurality of distances along the central axis of the vessel.

In step 130 a first ultrasound Doppler signal is obtained from a first distance from the pulse origin and in step 135 a second ultrasound Doppler signal is obtained from a second distance from the pulse origin.

The first and second Doppler signals are constructed from the ultrasound echoes received from the first and second measuring distance, respectively.

In the context of pulse wave velocity assessment, the maximum pulse wave velocity, $PWV_{max}$, governs the minimum time delay, $\Delta t_{min}$, that needs to be resolved by the system to provide an accurate estimation:

$$\Delta t_{min} > \frac{z_2 - z_1}{PWV_{max}}$$

where: $z_1$ is the first distance from the ultrasonic pulse origin; and $z_2$ is the second distance from the ultrasonic pulse origin. Put another way, $z_2-z_1$ is the distance between the first and second measurement points along the vessel.

To achieve a good resolution, $\Delta t_{min}$ must span several pulse transmissions of the ultrasonic transducer so that:

$$\Delta t_{min} \gg 1/f_{PRF}$$

where $f_{PRF}$ is the pulse rate frequency of the ultrasonic transducer, i.e. the number of ultrasound pulses generated per second.

In the example of renal denervation, the pulse wave velocity is expected to be up to 20 m/s. Taking this to be $PWV_{max}$ and choosing $z_1$=4 mm and $z_2$=8 mm results in $\Delta t_{min}$>0.2 ms, which would mean 16 ultrasound pulses would be generated at an example $f_{PRF}$ of 80 kHz. Thus, it is expected that there will be at least 16 successive ultrasound pulse transmissions worth of delay between when the velocity wave hits $z_1$ and when it hits $z_2$. It should be noted that choosing $z_1$ too small may cause the received signals, and so the velocity metric, to be affected by the presence of the intravascular device itself. Thus, $z_1$ should be chosen to given enough distance between the device and the measurement spot so as to reduce, or eliminate, such interference.

In pulsed Doppler processing, a Doppler signal is obtained by phase-quadrature demodulation of the detected pulse-echo signals, or radio-frequency (RF) data, obtained at various measurement depths $z_m$ that correspond to a certain time delay after each ultrasound pulse was transmitted.

Phase-quadrature demodulation (or complex demodulation) is equivalent to the separation of the in-phase (I) and quadrature (Q) components of the received signals, in order to demodulate it from the high-frequency band to the baseband. This function may be performed by the Doppler processor 28 described above with reference to FIG. 1. Phase-quadrature demodulation is further described in Loupas et al., "An Axial Velocity Estimator for Ultrasound Blood Flow Imaging, Based on a Full Evaluation of the Doppler Equation by Means of a Two-Dimensional Autocorrelation Approach", IEEE Transactions on Ultrasonics, Ferroelectrics, and Frequency Control, Vol. 42, No. 4, Jul. 1995.

The measurement depth and time delay are related to each other by the known speed of sound in the medium being imaged, such a blood in a vessel. Each ultrasound pulse transmission will provide one sample to the Doppler signal at each measurement depth.

In step 140, a first flow velocity metric is obtained based on the first ultrasound Doppler signal and in step 145 a second flow velocity metric is obtained based on the second ultrasound Doppler signal.

In Doppler ultrasound imaging, the received signals are used to determine the velocity of a given fluid. As the signals reflect from the fluid particles, they will receive a Doppler shift according to the direction of flow of the fluid, which may then be used to determine the velocity of the fluid at the received echo location.

In the case of a performing Doppler measurements within a blood vessel, the velocity of the blood will not be even and constant, but will have vary over time according to various physiological processes, such as the beating of the heart. This will cause the velocity of the blood to change in a certain way over a given period of time, such as over several seconds. This characteristic change in velocity will propagate through the vascular system at a certain speed, namely, the PWV.

By identifying this characteristic change in velocity at the two known measurement locations, and determining the time taken to occur at the second location after occurring at the first, it is possible to measure the PWV.

The characteristic change in velocity may be identified by a number of velocity metrics. The velocity metric measured at the first measurement position is referred to as the first velocity metric and the velocity metric measured at the second measurement position is referred to as the second velocity metric; however, the first and second velocity metrics may represent the same characteristic change in velocity.

In an example, the first flow velocity metric may be a first average velocity and the second flow velocity metric may be a second average velocity. More specifically, the flow velocity may be measured at the first and second measurement points over a predetermined length of time. When an average velocity, for example as measured over 1ms, appears at the second measurement location after having appeared at the first, meaning that the first and second velocity metrics match, it may be determined that the characteristic change in velocity has traversed the measurement distance.

The average velocities at the first and second measurement points may, for example, be assessed by the Kasai algorithm (as described in Kasai et al., "Real-Time Two-Dimensional Blood Flow Imaging Using an Autocorrelation Technique", IEEE Transactions on Sonics and Ultrasonics, Vol SU-32, No. 3, May 1985) or the Loupas algorithm (as described in Loupas et al., "An Axial Velocity Estimator for Ultrasound Blood Flow Imaging, Based on a Full Evaluation of the Doppler Equation by Means of a Two-Dimensional Autocorrelation Approach", IEEE Transactions on Ultrasonics, Ferroelectrics, and Frequency Control, Vol. 42, No. 4, Jul. 1995).

In another example, the first flow velocity metric may be a first distribution of flow velocities and the second flow velocity metric may be a second distribution of flow velocities. In other words, the velocities at the first and second measurement locations may be measured periodically, the length of the period may depend on the accuracy required by the application.

Each velocity value of the first and second velocity distributions may then be compared in order to calculate a plurality of time delays across the distributions. The time delays may then be averaged to arrive at the final time delay to be used to calculate the PWV.

In a further example, the obtaining of the first and second distributions of flow velocities may include obtaining a first and second frequency spectrum, respectively.

In other words, a frequency spectrum is obtained at each measurement depth, which in this case represent the distribution of flow velocities at $z_1$ and $z_2$. The frequency of the obtained Doppler signals will comprise a frequency shift compared to the originally generated ultrasound pulse, which is directly related to the flow velocity at the measurement point. As the velocity at a given measurement point changes over time, so will the frequency shift in the obtained Doppler signals, thereby resulting in a spectrum of different received frequencies. Frequency bins may then be taken to represent a given velocity, or range of velocities.

In existing systems, the peak flow velocity may be determined by a spectral Doppler approach, which involves the calculation of the frequency spectrum of the Doppler signals over an ensemble of ultrasound pulse transmissions, which in some applications may be up to 256 transmissions. A higher number of transmissions increases the velocity resolution that may be observed; however, it also reduces the time resolution over which differences in the velocity may be observed.

In such cases, the time resolution is not as critical as it is for the proposed PWV measurement method described above, where a significantly lower number of transmissions, such as 16, might be beneficial. Indeed, both approaches may be employed in parallel for a simultaneous flow velocity and PWV measurement from the same raw measurement data.

In step 150, a time delay is calculated based on the first flow velocity metric and the second flow velocity metric.

As discussed above, the time delay may be calculated based on an average first velocity at the first measurement point and an average second velocity at the second measurement point.

Alternatively, the time delay may be calculated by determining an individual time delay for each velocity measurement across a distribution of first and second velocity measurements and calculating an average time delay based on this. The individual velocity measurements may take the form of a range of velocities of a velocity distribution or a frequency bin of the spectrum of Doppler signal frequencies.

As discussed above, the change in velocity over time is likely to contain characteristic features, for example relating to a heartbeat cycle, as it propagates through the vascular system.

As such, the time delay may be calculated based on a comparison between a feature of the first distribution of velocities, referred to as a first feature, and a feature of the second distribution of velocities, referred to as a second feature. The first and second features need not be singular features, but may include a number of different features that appear in both the first and second velocity distributions.

By way of example, the first and second features may include one or more of: an instantaneous peak velocity; a pulse onset; a peak time; and a maximum acceleration. In particular, the instantaneous peak velocity represents the maximum flow velocity, which is typically found in the centre of the vessel lumen. This feature is less affected by irrelevant parts of the velocity distribution, such as slow velocities that may be representative of wall motion rather than blood flow.

The calculation of the time delay between the first and second velocity metrics $z_1$ and $z_2$ may be calculated using cross-correlation approaches.

Cross-correlation methods, which measure the similarity between two signals, may be performed directly on the obtained Doppler signals, prior to any frequency spectrum calculation. Thus, with this approach, no frequency spectrum needs to be calculated. Instead, a time delay representative of the pulse wave velocity is obtained by finding the time delay at which the Doppler signals between $z_1$ and $z_2$ provide the highest correlation.

In step 160, the pulse wave velocity is calculated based on the time delay.

As the distance between $z_1$ and $z_2$, x, is known and the time delay $\Delta t$ is calculated using one of the various methods laid out above, it is a simple matter to determine the PWV as:

$$PWV = \frac{x}{\Delta t}$$

In addition to the velocity metrics, a pressure metric may also be obtained within the vessel for use when calculating of the pulse wave velocity as stated above with reference to the equation:

$$PWV = \sqrt{\frac{1}{\rho D}}, \text{ with } D = \frac{dV}{VdP}$$

By calculating the PWV via two methods, it is possible to increase the accuracy of the final PWV and check quality of the velocity metric based measurement.

Figure 3:
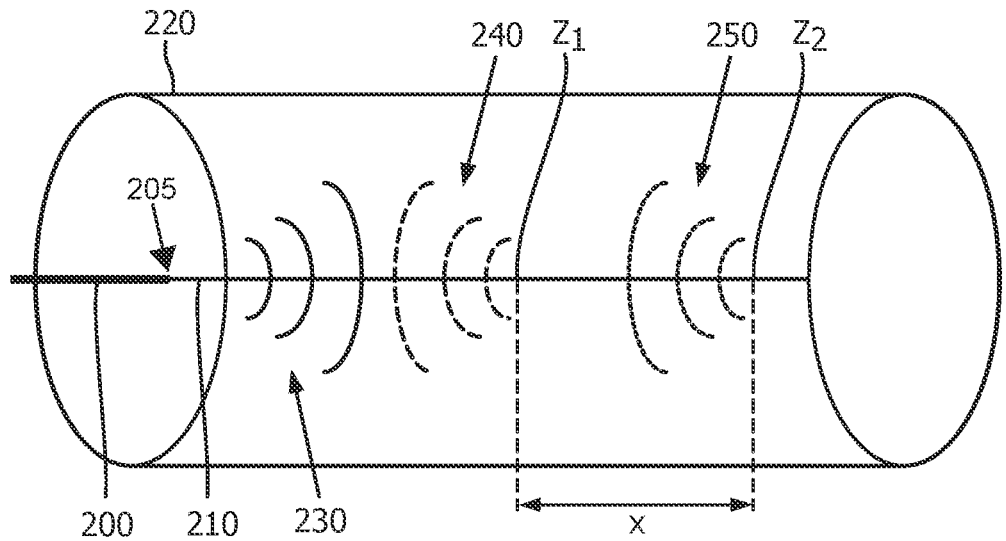
FIG. 3 shows a schematic representation of an intravascular device within a vessel.

FIG. 3 shows an intravascular device 200 aligned with the central axis 210 of a vessel 220.

The single sensor 205 of the intravascular device 200 generates a plurality of ultrasound pulses 230 and receives a plurality of echo signals 240 from a first measurement location, at a first distance $z_1$ from the device, and a plurality of echo signals 250 from a second measurement location, at a second distance $z_2$ from the device. The first and second distances are separated by distance, x.

The plurality of echo signals 240 from the first measurement location are used to form a first Doppler signal and the plurality of echo signals 250 from the second measurement location are used to form a second Doppler signal.

Figure 4:
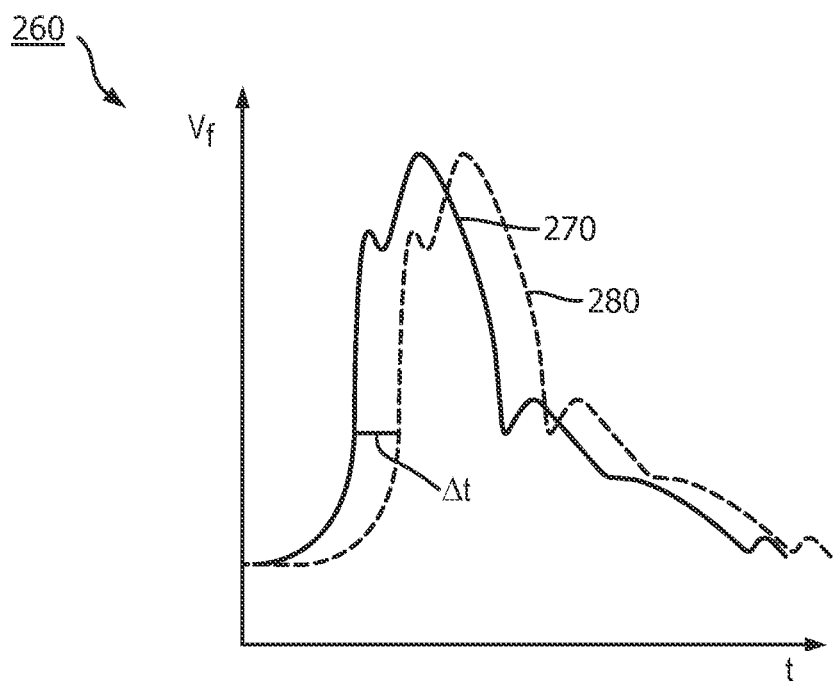
FIG. 4 shows plots of velocity against time for a first and second measurement location.

FIG. 4 shows a graph 260 of flow velocity, $v_f$, against time.

The graph shows a first velocity distribution plot 270 and a second velocity distribution plot 280, acquired from the first and second Doppler signals, respectively. As can be seen from the Figure, the two plots are the same shape with the second plot shifted in time. This shift in time represents the time taken for a pulse to travel along the vessel and so is indicative of the PWV. By comparing the first and second plots, it is possible to derive a time delay, $\Delta t$, which may then be used in combination with the known distance, x, to derive the PWV.

Figure 5:
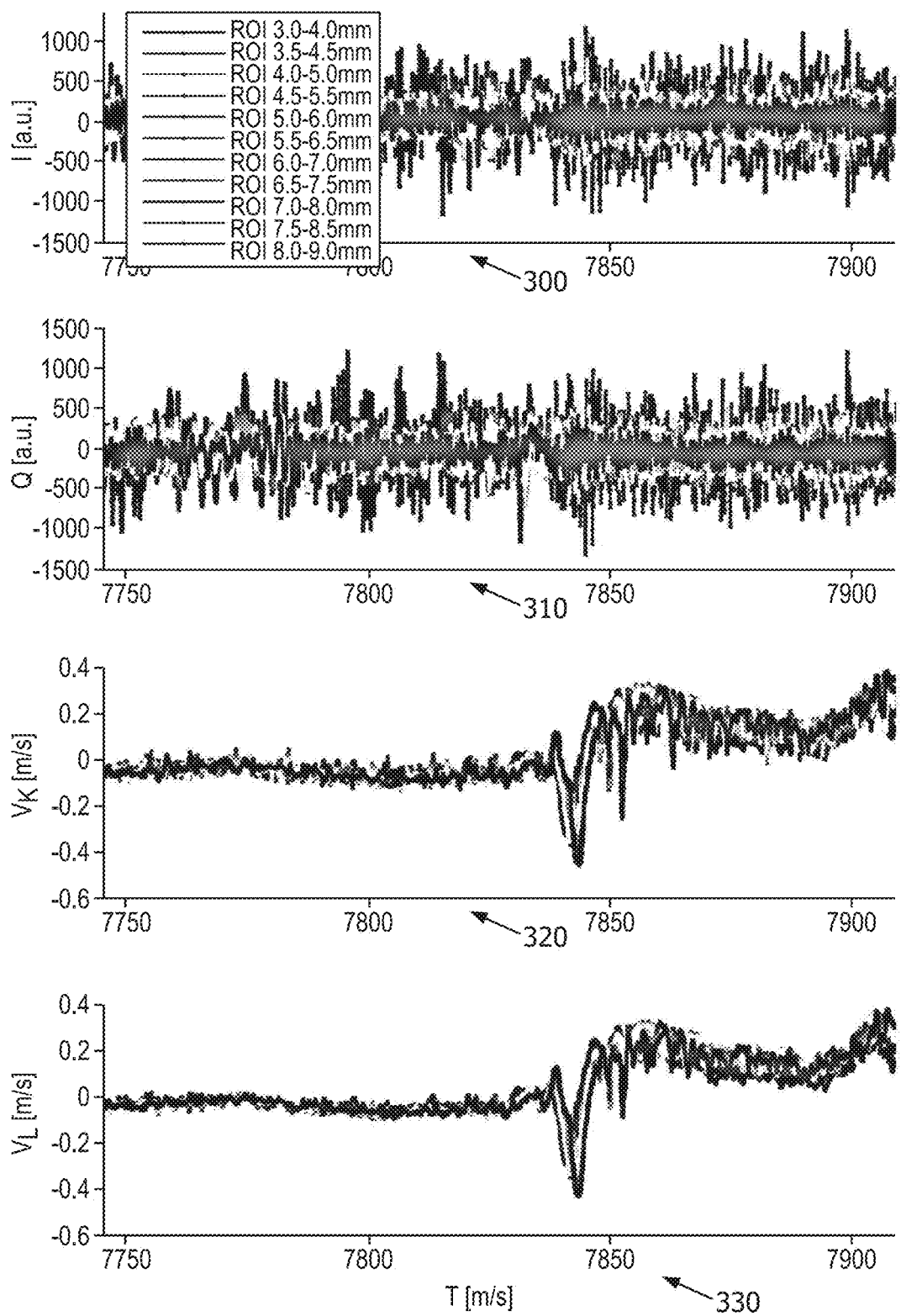
FIG. 5 shows a series of graphs relating to a plurality of ultrasound Doppler signal obtained at various depths.
Figure 6:
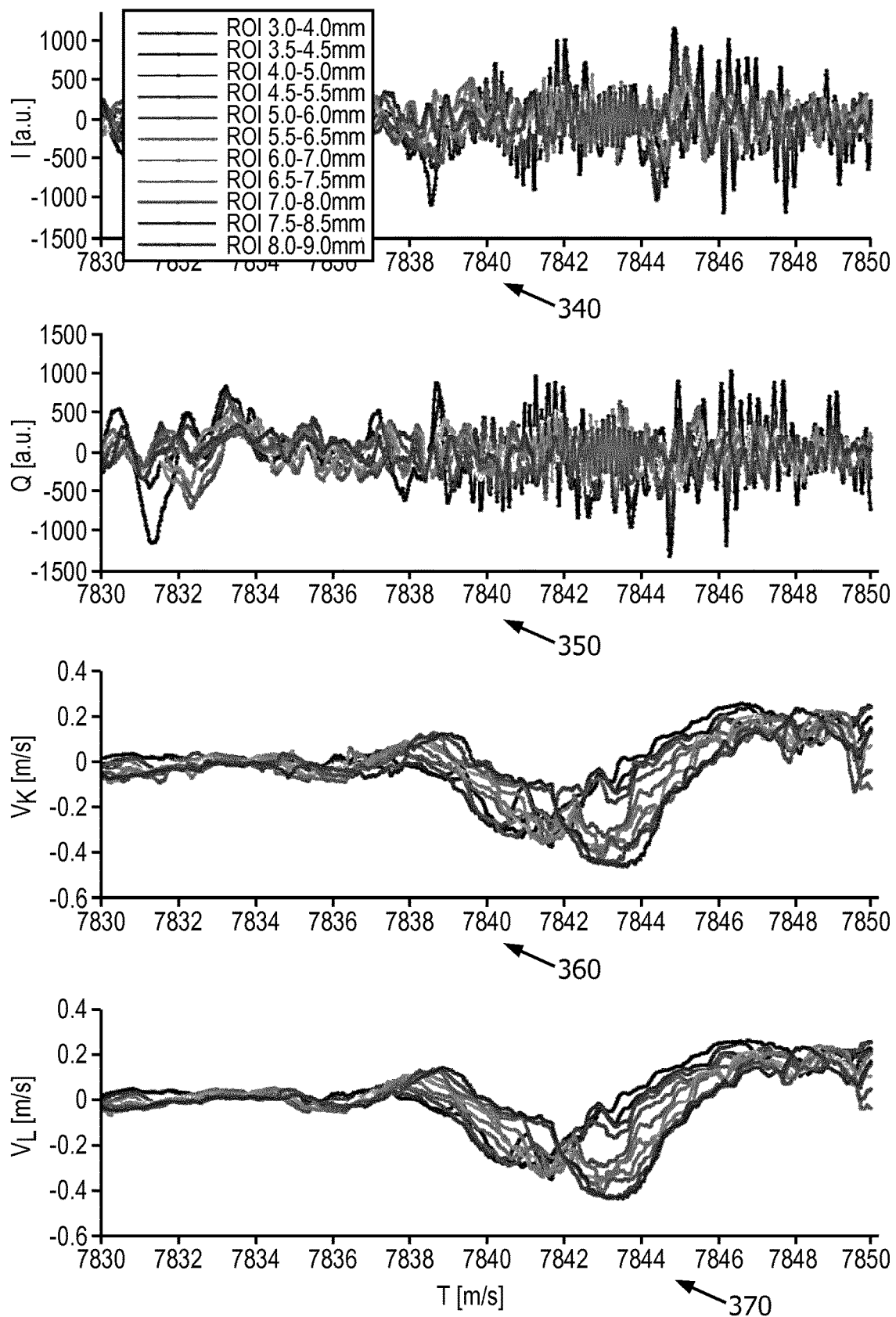
FIG. 6 shows a time window of the graphs of FIG. 5.

FIGS. 5 and 6 each show 4 graphs relating to the obtained Doppler signals over time, T, wherein the graphs of FIG. 6 show a 20 ms section of the plots of FIG. 5 between 7830 ms and 7850 ms.

Looking to FIG. 5, the first graph 300 and the second graph 310 show plots of the separated I and Q components of the received ultrasound Doppler signals, respectively. In other words, the first and second graphs show the I and Q components of a Doppler signal following phase-quadrature demodulation. Each plot on the first and second graphs represents a different measurement depth, or region of interest (ROI).

Every time point of the plots result from one pulse transmission by the intravascular device. The pulse repetition rate in this example is 50 kHz and is, therefore, the sampling frequency of these signals and, eventually, also of the estimated velocity signal from which the PWV is calculated. The third graph 320 and fourth graph 330 show the instantaneous velocity as estimated by the Kasai (third graph) and Loupas (fourth graph) algorithms. In other words, the third graph shows the estimated Kasai velocity, $V_K$, and the fourth graphs shows the estimated Loupas velocity, $V_L$. These algorithms estimate the instantaneous average frequency in the I and Q signals, related directly to the average flow velocity within the vessel by the Doppler equation. These two graphs indicate that the velocity changes from near 0 to roughly 0.2 m/s just before 7850 ms. This velocity change results from a pulse wave, and, looking closely at the signals, it can be seen that the velocity changes at low depths (3-4 mm) before it does so at higher depths (eg 8-9 mm). In other words, there is an observable time delay between the pulse wave reaching the measurement depths of 3-4 mm and the measurement depths of 8-9 mm.

FIG. 6 shows the graphs of FIG. 5 between times 7830 ms and 7850 ms. The fifth graph 340 corresponds to the first graph 300. The sixth graph 350 corresponds to the second graph 310. The seventh graph 360 corresponds to the third graph 320. The eighth graph 370 corresponds to the fourth graph 330.

These graphs show the time around the arrival of the pulse wave, from which it can be seen, in the seventh 360 and eighth 370 graphs that there is a time delay of a few milliseconds between the arrival of the velocity wave between the different depths. Further, the fifth 340 and sixth 350 graphs show the change in the I and Q signals that results from the velocity wave, where the high-frequency components appear upon the arrival of the velocity wave near 7840 ms.

Figure 7:
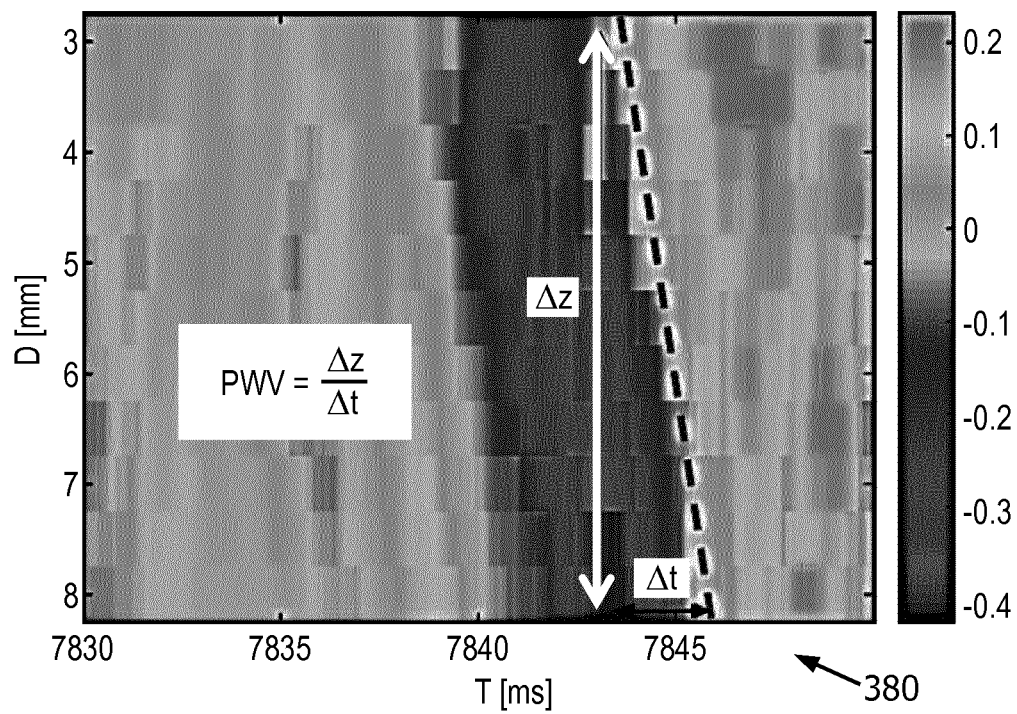
FIG. 7 shows a graphical representation of an estimated Loupas velocity.

FIG. 7 shows an alternative graphical representation 380 of the Loupas velocity shown in the eighth 370 graph of FIG. 6.

The velocity wave is shown by the shading as a function of time, T, (horizontal axis) and distance from the transducer, or depth D, (vertical axis). Graphically, the pulse wave velocity may be interpreted from this image by drawing a line along the phase of the velocity wave. The slope of this line, which is equivalent to $$\frac{\Delta z}{\Delta t},$$

indicates the pulse wave velocity.

Figure 8:
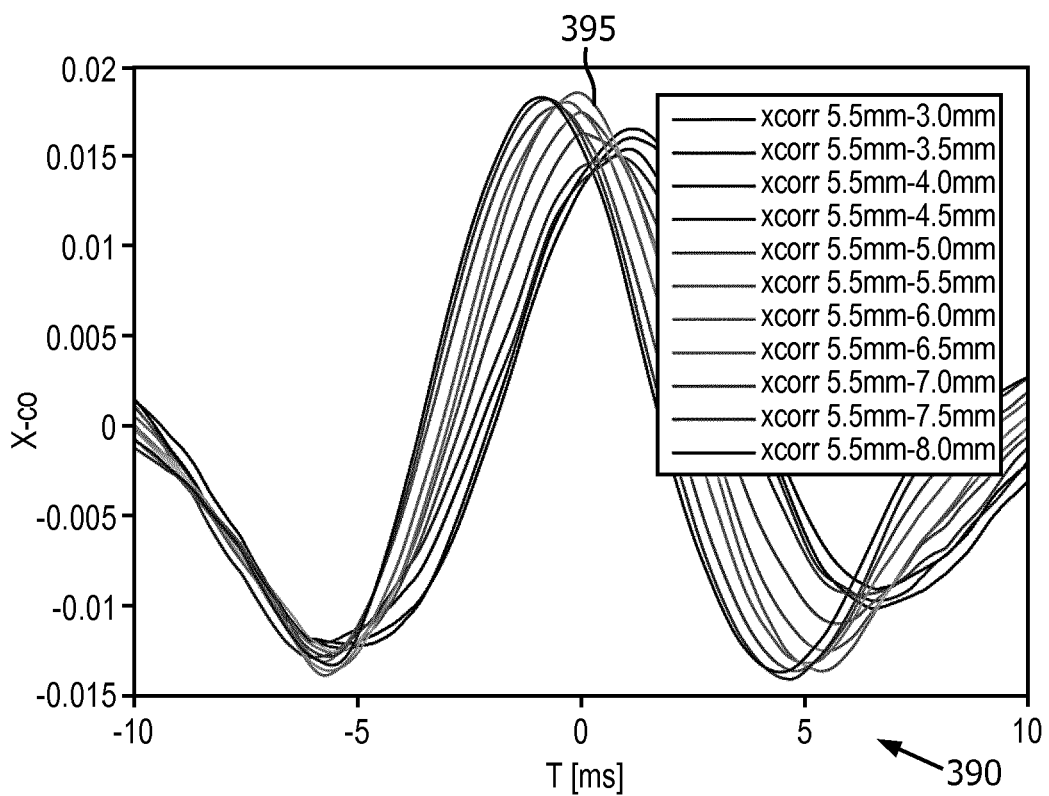
FIG. 8 shows a graph of cross-covariance for velocity signals obtained at different measurement depths.

FIG. 8 shows a graph 390 of the cross-covariance, X-co, which is equivalent to the cross-correlation after subtracting the average from the signal, against time, T. The cross-covariance is calculated between velocity signals obtained at the 5.5-6.5 mm measurement depths, identifiable by the plot 395 having a peak centered at 0 ms, and those obtained at the remaining measurement depths. The location of the peak in the cross-covariance is indicative of the delay between the arrival of the pulse waves between the various measurement depths. As an example, the pulse wave at the 8-9 mm depth is most closely correlated to that at the 5.5-6.5 mm depth when the latter is delayed by about 1 ms. Further, the pulse wave at the 3-4 mm depth is optimally correlated to that at the 5.5-6.5 mm depth when the former is delayed by about 1.2 ms.

Figure 9:
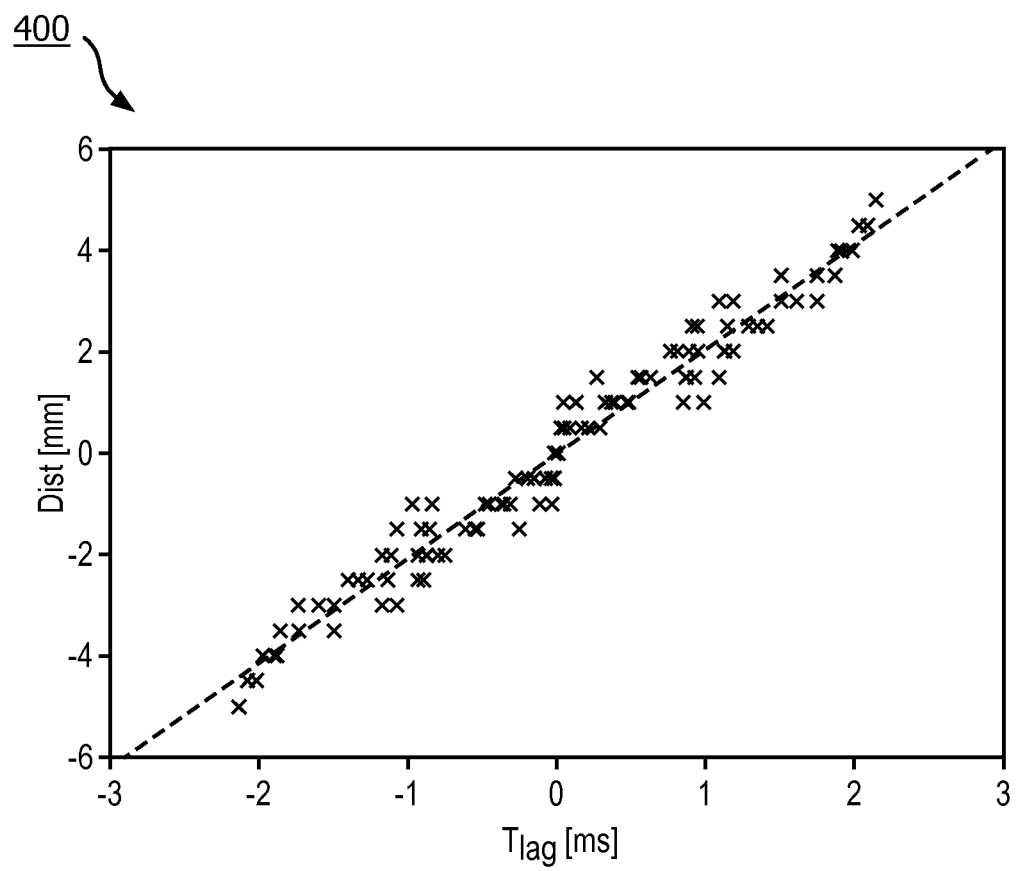
FIG. 9 shows a graph of measurement depth against maximum cross-covariance.

FIG. 9 shows a graph 400 of the optimal lag times, $T_{lag}$, for maximum cross-covariance between any two measurement depths (on the x-axis) plotted against the known distance between the measurement depths (on the y-axis). The data points convey a trend indicative of the pulse wave velocity shown by the dotted line. The pulse wave velocity may be estimated as the slope of this line, resulting, in this example, in a value of 2.1 m/s.

The intravascular device may include a number of ultrasound transducer elements, in which case, the intravascular ultrasonic pulses may be directed along the central axis of the vessel using electronic beam steering and/or electronic beam focusing. In this way, the measurements may be made less sensitive to the orientation of the intravascular device.

Electronic beam steering and focussing may be applied so as to optimally align the ultrasound beam with the flow direction in order to ensure that the axis over which the pulse wave velocity is assessed corresponds with the axis of pulse wave propagation.

This may be implemented by optimizing the ultrasound beam angle so as to maximize the strength of the Doppler signal, for example, at the point where maximum flow velocity. Optimization of the beam angle may be performed in an iterative and/or adaptive manner.

Further, the measurements may be performed with two separate ultrasound transducers that may be implemented on two separate intravascular devices. This may provide a greater freedom in choosing the distance between the two measurement locations.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A system for performing intravascular pulse wave velocity measurements, the system comprising:
   an intravascular ultrasound device adapted to:
      generate, using a single sensor, a plurality of intravascular ultrasonic pulses at a pulse origin, wherein the plurality of intravascular ultrasonic pulses are directed along a vessel;
      for each of the plurality of intravascular ultrasonic pulses, receive a plurality of echoes from a plurality of distances relative to the pulse origin, using the single sensor; and
   a processor adapted to:
      obtain a first ultrasound Doppler signal from a first distance relative to the pulse origin based on a plurality of echoes;
      identify a change in velocity at the first distance based on the first ultrasound Doppler signal;
      obtain a second ultrasound Doppler signal from a second distance relative to the pulse origin based on the plurality of echoes;
      identify the change in velocity at the second distance based on the second ultrasound Doppler signal;
      determine a time delay based on the change in velocity at the first distance and the change in velocity at the second distance, wherein the time delay corresponds to a time for the change in velocity to propagate from the first distance to the second distance;
      calculate a pulse wave velocity based on the time delay; and provide an output based on the pulse wave velocity to a display.

2. The system according to claim 1, wherein the single sensor comprises:
a single ultrasound transducer element; or an array of ultrasound transducer elements.

3. The system of claim 1, wherein, to determine the time delay, the processor is adapted to perform cross-correlation between the first ultrasound Doppler signal and the second ultrasound Doppler signal.

4. The system of claim 1, wherein, to identify the change in velocity at the first distance, the processor is adapted to obtain a first flow velocity metric based on the first ultrasound Doppler signal, and wherein, to identify the change in velocity at the second distance, the processor is adapted to obtain a second flow velocity metric based on the second ultrasound Doppler signal.

5. The system of claim 4, wherein the first flow velocity metric comprises a first average velocity and the second flow velocity metric comprises a second average velocity.

6. The system of claim 4, wherein the first flow velocity metric comprises a first distribution of flow velocities and the second flow velocity metric comprises a second distribution of flow velocities.

7. The system of claim 6, wherein the first distribution of flow velocities comprises a first frequency spectrum and the second distribution of flow velocities comprises a second frequency spectrum.

8. The system of claim 6, wherein, to determine the time delay, the processor is adapted to:
for each velocity value of the first distribution of flow velocities and second distribution of flow velocities, calculate an individual time delay of a plurality of individual time delays; and
calculate an average time delay based on the plurality of individual time delays.

9. The system of claim 6,
wherein, to identify the change in velocity at the first distance, the processor is adapted to extract a first feature of the first distribution of flow velocities;
wherein, to identify the change in velocity at the second distance, the processor is adapted to extract a second feature of the second distribution of flow velocities; and
wherein, to determine the time delay, the processor is adapted to:
calculate the time delay based on the first feature and the second feature.

10. The system of claim 9, wherein the first and second feature comprises one or more of:
an instantaneous peak velocity;
a pulse onset;
a peak time;
a maximum acceleration; and
an instantaneous average velocity.

11. The system of claim 6, wherein, to determine the time delay, the processor is adapted to perform cross-correlation between the first distribution of flow velocities and the second distribution of flow velocities.

12. The system of claim 1, wherein the system is further configured to obtain a pressure metric and wherein the calculation of the pulse wave velocity is based on the time delay and the pressure metric.

13. The system according to claim 1, wherein the processor is adapted to use electronic beam steering and/or electronic beam focusing to control the intravascular ultrasound device to generate the plurality of intravascular ultrasonic pulses.

14. A method of calculating a pulse wave velocity, the method comprising:
generating, using a single sensor, a plurality of intravascular ultrasonic pulses at a pulse origin, wherein the plurality of intravascular ultrasonic pulses are directed along a vessel;
for each of the plurality of intravascular ultrasonic pulses, receiving a plurality of echoes from a plurality of distances relative to the pulse origin, using the single sensor;
obtaining a first ultrasound Doppler signal from a first distance relative to the pulse origin based on a plurality of echoes;
identifying a change in velocity at the first distance based on the first ultrasound Doppler signal;
obtaining a second ultrasound Doppler signal relative to a second distance from the pulse origin based on the plurality of echoes;
identifying the change in velocity at the second distance based on the second ultrasound Doppler signal;
determining a time delay based on the change in velocity at the first distance and the change in velocity at the second distance, wherein the time delay corresponds to a time for the change in velocity to propagate from the first distance to the second distance;
calculating a pulse wave velocity based on the time delay; and
outputting the pulse wave velocity to a display.

15. A non-transitory computer-readable storage medium comprising a computer program which is adapted, when said computer program is run on a computer, to implement a method of calculating a pulse wave velocity on a system according to claim 1.

* * * * *